US012611674B2

(12) United States Patent
Litten et al.

(10) Patent No.: US 12,611,674 B2
(45) Date of Patent: Apr. 28, 2026

(54) FLUID DELIVERY CONSUMABLE FOR DELIVERING A FLUID TO A BIOREACTOR

(71) Applicant: Oribiotech LTD, London (GB)

(72) Inventors: Neil Litten, Reading (GB); Richard Smith, Cambridgeshire (GB); Farlan Veraitch, London (GB); William Raimes, London (GB)

(73) Assignee: Oribiotech LTD, London (GB)

( * ) Notice: Subject to any disclaimer, the term of this patent is extended or adjusted under 35 U.S.C. 154(b) by 653 days.

(21) Appl. No.: 17/905,984

(22) PCT Filed: Mar. 9, 2021

(86) PCT No.: PCT/GB2021/050579
§ 371 (c)(1),
(2) Date: Sep. 9, 2022

(87) PCT Pub. No.: WO2021/181079
PCT Pub. Date: Sep. 16, 2021

(65) Prior Publication Data
US 2023/0108218 A1       Apr. 6, 2023

(30) Foreign Application Priority Data

Mar. 9, 2020    (GB) ...................................... 2003403
Dec. 16, 2020    (GB) ...................................... 2019859

(51) Int. Cl.
*B01L 3/00*        (2006.01)
*C12M 1/00*        (2006.01)
(Continued)

(52) U.S. Cl.
CPC ................ *B01L 3/563* (2013.01); *B01L 3/52* (2013.01); *C12M 1/10* (2013.01); *C12M 1/268* (2013.01);
(Continued)

(58) Field of Classification Search
None
See application file for complete search history.

(56) References Cited

U.S. PATENT DOCUMENTS 2,847,996 A       8/1958   Cohen et al.
3,901,402 A *    8/1975   Ayres .................. B01L 3/50215
604/218
(Continued)

FOREIGN PATENT DOCUMENTS

EP            0711571 B1      12/1999
GB            2580356 A        7/2020
(Continued)

OTHER PUBLICATIONS

International Search Report for International Application No. PCT/GB2021/050579, mailed Jun. 9, 2021, 4 pages.
(Continued)

*Primary Examiner* — Brian R Gordon
(74) *Attorney, Agent, or Firm* — TraskBritt

(57) ABSTRACT

The present disclosure provides a fluid delivery consumable for delivering a fluid dose to a bioreactor. The fluid delivery consumable includes a vial for holding the fluid dose, a plunger, and a connector. The vial includes an outlet and an open end opposite to the outlet. The plunger is engaged with the open end and operable to urge the fluid dose toward the outlet. The connector is proximal to the outlet and attachable to the bioreactor. The connector is adapted to transfer the fluid dose from the vial to the bioreactor when the plunger is operated to urge the fluid dose out of the outlet of the vial.

15 Claims, 13 Drawing Sheets

(51) Int. Cl.

| | |
|---|---|
| *C12M 1/10* | (2006.01) |
| *C12M 1/12* | (2006.01) |
| *C12M 1/26* | (2006.01) |
| *C12M 3/00* | (2006.01) |

(52) U.S. Cl.

CPC ............ *C12M 23/34* (2013.01); *C12M 23/42* (2013.01); *C12M 23/46* (2013.01); *C12M 23/50* (2013.01); *C12M 29/00* (2013.01); *C12M 33/04* (2013.01); *C12M 37/04* (2013.01); *B01L 2200/0689* (2013.01); *B01L 2300/044* (2013.01); *B01L 2300/123* (2013.01); *B01L 2400/0478* (2013.01); *C12M 1/007* (2013.01); *C12M 23/26* (2013.01); *C12M 23/40* (2013.01)

(56) References Cited

U.S. PATENT DOCUMENTS

| | | | |
|---|---|---|---|
| 4,105,500 A * | 8/1978 | Libman | C12M 33/02 |
| | | | 435/39 |
| 4,192,919 A * | 3/1980 | Raghavachari .. | A61B 5/150717 |
| | | | D24/117 |
| 4,238,568 A | 12/1980 | Lynn | |
| 5,056,464 A * | 10/1991 | Lewis | C12M 21/10 |
| | | | 119/6.8 |
| 5,164,796 A | 11/1992 | Di Guiseppi et al. | |
| 5,652,143 A * | 7/1997 | Gombrich | C12M 23/34 |
| | | | 435/304.2 |
| 5,658,531 A * | 8/1997 | Cope | G01N 21/0303 |
| | | | 422/430 |
| 5,761,885 A | 6/1998 | Hansen | |
| 6,432,697 B1 | 8/2002 | Tice et al. | |
| 6,716,187 B1 * | 4/2004 | Jorgensen | A61M 1/029 |
| | | | 604/407 |
| 8,268,263 B2 * | 9/2012 | Campbell | B01L 3/563 |
| | | | 141/330 |
| 8,415,144 B2 | 4/2013 | Wilson et al. | |
| 9,145,581 B1 * | 9/2015 | Lai | C12Q 1/6806 |
| 9,180,252 B2 * | 11/2015 | Gelblum | A61M 5/2425 |
| 9,380,973 B2 | 7/2016 | Fletcher et al. | |
| 2002/0025547 A1 | 2/2002 | Rao | |
| 2003/0060749 A1 | 3/2003 | Aneas | |
| 2003/0143727 A1 | 7/2003 | Chang | |
| 2006/0178644 A1 * | 8/2006 | Reynolds | A61J 1/2093 |
| | | | 604/232 |
| 2007/0224676 A1 | 9/2007 | Haq | |
| 2007/0254356 A1 | 11/2007 | Wilson et al. | |
| 2008/0311650 A1 | 12/2008 | Jakob et al. | |
| 2009/0191620 A1 | 7/2009 | Martin et al. | |
| 2010/0077843 A1 * | 4/2010 | Doraisamy | B01L 3/5029 |
| | | | 73/864.01 |
| 2010/0083774 A1 * | 4/2010 | Schmiedl | G01F 11/029 |
| | | | 29/428 |
| 2010/0093551 A1 * | 4/2010 | Montagu | G01N 33/491 |
| | | | 210/120 |
| 2011/0076756 A1 | 3/2011 | Wright | |
| 2012/0083029 A1 | 4/2012 | Tsumura et al. | |
| 2012/0202193 A1 * | 8/2012 | Heinrich | A61B 10/0096 |
| | | | 422/534 |
| 2013/0029324 A1 * | 1/2013 | Rajagopal | B01L 3/502 |
| | | | 435/8 |
| 2013/0281940 A1 | 10/2013 | Gelblum et al. | |
| 2014/0010740 A1 * | 1/2014 | Anitua Aldecoa | |
| | | | A61B 5/150908 |
| | | | 422/570 |
| 2014/0048556 A1 * | 2/2014 | Pearcy | A61M 5/31511 |
| | | | 222/137 |
| 2014/0076454 A1 | 3/2014 | Kjar | |
| 2014/0170644 A1 * | 6/2014 | Hadayer | G01N 1/08 |
| | | | 435/6.1 |
| 2015/0151035 A1 * | 6/2015 | Huemer | B01L 3/5635 |
| | | | 210/321.6 |
| 2015/0173660 A1 * | 6/2015 | Choon Meng ... | A61B 5/150732 |
| | | | 600/583 |
| 2015/0252317 A1 | 9/2015 | Lipkens et al. | |
| 2015/0368602 A1 | 12/2015 | Galliher et al. | |
| 2016/0152935 A1 | 6/2016 | Roosloot et al. | |
| 2016/0265022 A1 * | 9/2016 | Yang-Woytowitz | |
| | | | A61J 1/1418 |
| 2016/0279551 A1 * | 9/2016 | Foucault | G01N 33/491 |
| 2018/0257051 A1 * | 9/2018 | De Haan | B01F 33/844 |
| 2018/0362910 A1 | 12/2018 | Bores et al. | |
| 2019/0030527 A1 * | 1/2019 | Walsh | B01L 3/5021 |
| 2019/0046977 A1 | 2/2019 | Ronsick et al. | |
| 2019/0062681 A1 | 2/2019 | Fan et al. | |
| 2020/0123493 A1 | 4/2020 | Schndube et al. | |
| 2020/0190457 A1 | 6/2020 | Veraitch et al. | |
| 2022/0154245 A1 * | 5/2022 | Ishimaru | C12Q 1/06 |
| 2025/0041844 A1 * | 2/2025 | Sia | A61J 1/201 |

FOREIGN PATENT DOCUMENTS

| | | |
|---|---|---|
| GB | 2590523 B | 12/2021 |
| JP | 63-503201 A | 11/1988 |
| JP | 2008-237203 A | 10/2008 |
| JP | 2020-500036 A | 1/2020 |
| JP | 2020-054392 A | 4/2020 |
| WO | 87/02252 A1 | 4/1987 |
| WO | 87/06952 A1 | 11/1987 |
| WO | 2008/068502 A1 | 6/2008 |
| WO | 2009/032645 A1 | 3/2009 |
| WO | 2009/093995 A1 | 7/2009 |
| WO | 2010/024906 A1 | 3/2010 |
| WO | 2011/144561 A1 | 11/2011 |
| WO | 2013/036429 A2 | 3/2013 |
| WO | 2015/187518 A1 | 12/2015 |
| WO | 2016/185221 A1 | 11/2016 |
| WO | 2018/087558 A1 | 5/2018 |
| WO | 2019/199406 A1 | 10/2019 |
| WO | 2021/123760 A1 | 12/2020 |
| WO | 2021/123762 A1 | 6/2021 |

OTHER PUBLICATIONS

International Written Opinion for International Application No. PCT/GB2021/050579, mailed Jun. 9, 2021, 6 pages.

United Kingdom Patent Examination Report for United Kingdom Patent Application No. GB2103244.6 , dated Feb. 17, 2022, 6 pages.

United Kingdom Patent Examination Report for United Kingdom Patent Application No. GB2103244.6 , dated May 25, 2022, 3 pages.

United Kingdom Search Report for United Kingdom Patent Application No. GB2019859.4 , dated Jun. 9, 2021, 3 pages.

United Kingdom Search Report for United Kingdom Patent Application No. GB2103244.6 , dated Aug. 19, 2021, 6 pages.

European Communication pursuant to Article 94(3) EPC for European Application No. 23178337.4, dated Oct. 23, 2024, 6 pages.

European Search Report Opinion for European Application No. 23178337.4, dated Oct. 2, 2023, 4 pages.

Japanese Notice of Refusal for Application No. 2022-554361 dated Jun. 3, 2025, 10 pages with machine translation.

* cited by examiner

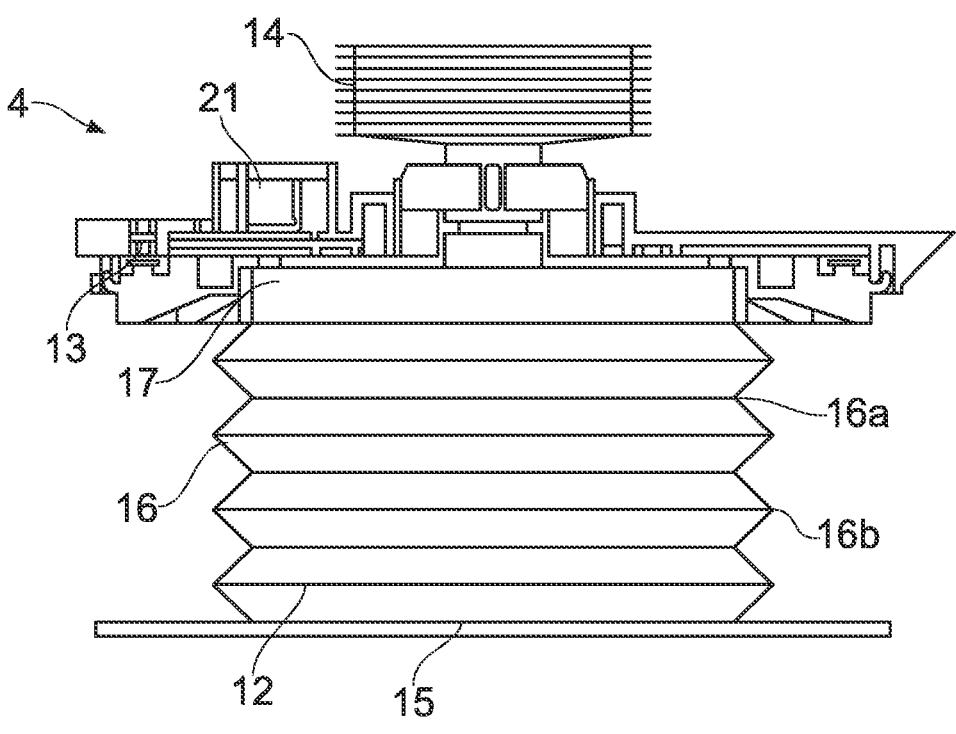
FIG. 3
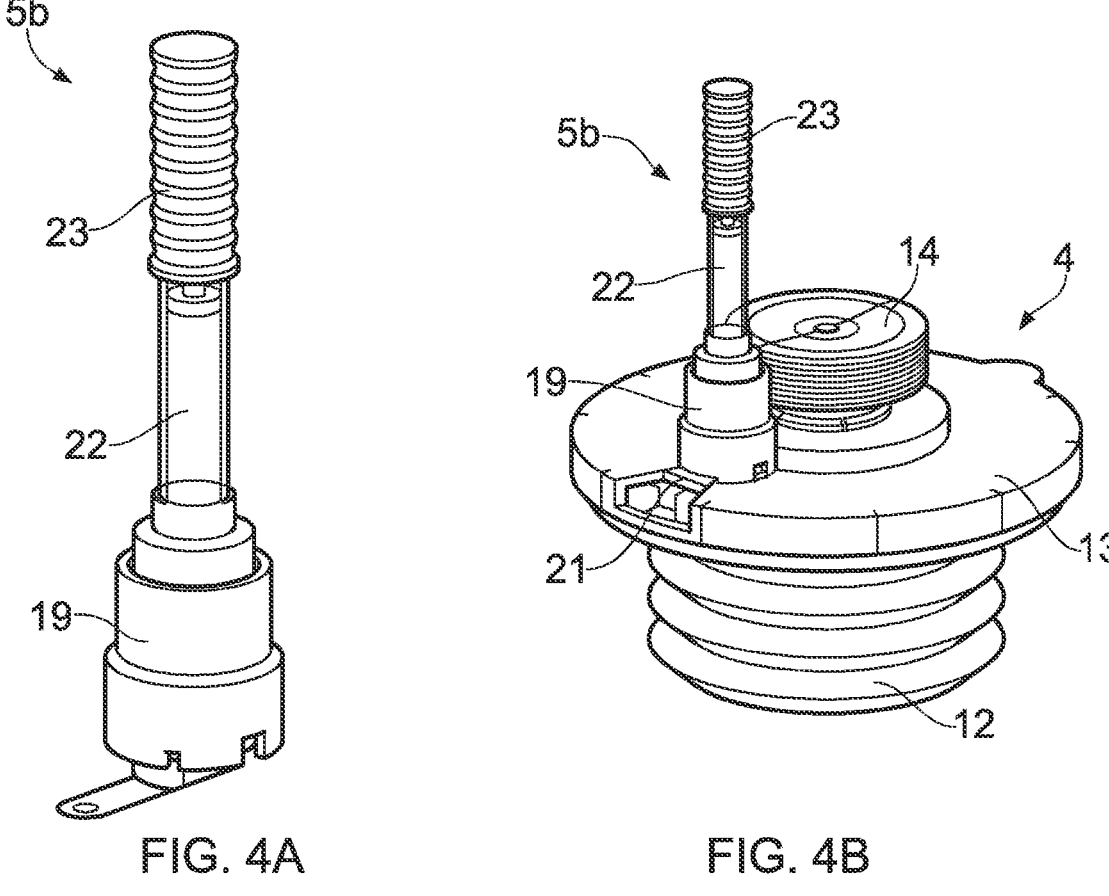
FIG. 4A                    FIG. 4B

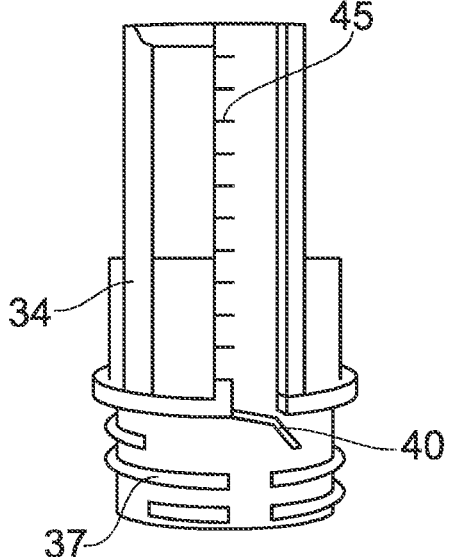
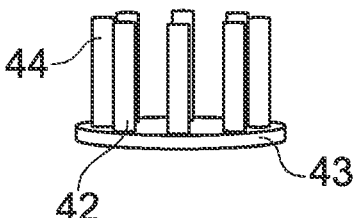
FIG. 10

FLUID DELIVERY CONSUMABLE FOR DELIVERING A FLUID TO A BIOREACTOR

CROSS-REFERENCE TO RELATED APPLICATIONS

This application is a national phase entry under 35 U.S.C. § 371 of International Patent Application PCT/GB2021/050579, entitled "FLUID DELIVERY CONSUMABLE FOR DELIVERING A FLUID TO A BIOREACTOR," filed Mar. 9, 2021, designating the United States of America and published as International Patent Publication WO 2021/181079 A1 on Sep. 16, 2021, which claims the benefit under Article 8 of the Patent Cooperation Treaty to Great Britain Patent Application Serial Nos. 2003403.9, filed Mar. 9, 2020, and 2019859.4, filed Dec. 16, 2020.

TECHNICAL FIELD

This disclosure relates to a fluid delivery consumable for delivering a fluid dose to a bioreactor. The bioreactor is suitable for performing one or more unit operations in a cell processing method, for example, in cell and/or gene therapy manufacturing processing. The fluid delivery consumable is operable to transfer a fluid dose, for example, a magnetic bead suspension or virus suspension, from the fluid delivery consumable to the bioreactor.

BACKGROUND

Cell and gene therapy manufacturing processes are often complex and include manual or semi-automated steps across several devices. Equipment systems used in various steps, or unit operations, of cell-based therapeutic products (CTP) manufacturing may include devices for various functions. These various functions may be, for example, cell collection, cell isolation, cell selection, cell expansion, cell washing, volume reduction, cell storage or transportation. The unit operations can vary immensely based on the manufacturing model (i.e., autologous versus allogenic), cell type, intended purpose, among other factors. In addition, cells are "living" entities sensitive to even the simplest manipulations, for example, such as differences in a cell transferring procedure. The role of cell manufacturing equipment in ensuring scalability and reproducibility is an important factor for cell and gene therapy manufacturing.

In addition, cell-based therapeutic products (CTP) have gained significant momentum thus there is a need for improved cell manufacturing equipment for various cell manufacturing procedures. These manufacturing procedures, may include, for example, stem cell enrichment, generation of chimeric antigen receptor (CAR) T cells, and various cell manufacturing processes such as collection, purification, gene modification, incubation, recovery, washing, infusion into a patient, or freezing.

The culture or processing of cells typically requires the use of a device to hold the cells, for example, in an appropriate culture medium when culturing the cells. The known devices include shaker flasks, roller bottles, T-flasks, bags and the like. Such devices are typically required to be connected to other devices, such as containers, interfaces or the like, so that various media may be introduced to, or removed from, the device holding the cells. Typically, cells in a culture medium can be added to the device from a flexible bag that is attached using a connecting tube. Alternatively, cells can be transferred by a pipette or by a syringe.

The production of autologous CAR T cells is carried out by a variety of manufacturing approaches all comprising the same common steps. First, the patient's white blood cells (WBCs) are isolated by leukapheresis and washed. Then, the T cells are activated, transduced with the CAR transgene, expanded to the required cell numbers for therapy, formulated and filled. After quality control testing and preparatory lymphodepleting chemotherapy for the patient, the product is injected into the patient.

BRIEF SUMMARY

In accordance with the present disclosure there is provided a fluid delivery consumable for delivering a fluid dose to a bioreactor. The fluid delivery consumable comprising:
  a vial for holding the fluid dose, the vial having an outlet and an open end opposite to the outlet,
  a plunger engaged with the open end and operable to urge the fluid dose toward the outlet, and
  a connector proximal to the outlet, the connector being attachable to the bioreactor such that operation of the plunger moves the fluid dose from the vial to the bioreactor.

In examples, the fluid delivery consumable may further comprise a seal arranged within the outlet of the vial to seal the outlet. In examples, the connector may comprise a hollow needle movable to pierce the seal to form a fluid connection with the vial. In examples, the seal may comprise a septum seal. In examples, the connector may comprise an actuator operable to move the needle to pierce the seal. In examples, the connector may comprise a first housing portion and a second housing portion, and wherein the actuator is operable to collapse the first housing portion relative to the second housing portion such that the hollow needle pierces the seal. In examples, the connector may be configured such that the hollow needle engages the bioreactor when the first housing portion collapses relative to the second housing portion.

In examples, the connector may further comprise an end seal arranged at an opposite end of the connector to the vial. The hollow needle may be arranged to pierce the end seal when the first housing portion is collapsed relative to the second housing portion.

In examples, the fluid delivery consumable may further comprise a collar attached to an end of the vial proximal to the outlet, the connector being attached to the collar. In examples, the collar may surround the end of the vial, including the outlet. In examples, the fluid delivery consumable may further comprise a lock ring shaped to engage a recess of the vial to secure the collar to the vial. In examples, the connector may be threadingly attached to the collar. In examples, the fluid delivery consumable may further comprise a clip member arranged to prevent detachment of the connector from the collar after the connector has been attached to the collar.

In examples, the collar or the connector may comprise the clip member, and wherein the clip member is arranged to engage a recess on the other of the collar or the connector when the connector has been attached to the collar to prevent rotation of the connector relative to the collar after the connector has been attached to the collar.

In examples, the fluid delivery consumable may further comprise a gaiter arranged to surround the plunger between the open end of the vial and a top end of the plunger. In examples, the gaiter may comprise a collapsible wall arranged to collapse as the plunger is actuated. In examples, the gaiter may be sealingly attached to the vial and the plunger to provide a sealed cover for the plunger.

In examples, the fluid delivery consumable may further comprise a cap attached to the top end of the plunger. The gaiter may be attached to the cap, and the cap may be larger than the open end of the vial such that the gaiter comprises a frustrum-shaped wall. The frustrum-shaped wall may be a frustoconical wall. In examples, the frustrum-shaped wall may comprise at least one inward fold and at least one outward fold arranged such that the frustrum-shaped wall is collapsible.

In examples, the plunger or the cap may comprise an engaging feature that is engageable for actuating the plunger.

In examples, the plunger may comprise a piston adapted to seal against an internal surface of the vial.

In examples, the vial may comprise a glass vial.

In examples, the fluid dose may comprise a plurality of magnetic particles in a fluid suspension. In examples, the fluid dose may comprise a virus suspension. In examples, the fluid dose may comprise a non-magnetic activated agent, for example, nanoparticles such as T Cell TransAct™ reagent. In examples, the fluid dose may comprise a growth factor, such as a concentrated growth factor, for example, cytokines.

BRIEF DESCRIPTION OF THE DRAWINGS

Embodiments of the disclosure are further described hereinafter with reference to the accompanying drawings, in which:

FIG. 3 illustrates the bioreactor;

FIGS. 4A and 4B show an example of a fluid delivery consumable attaching to the bioreactor;

FIG. 10 shows the collar and lock ring of the fluid delivery consumable of FIG. 6;

DETAILED DESCRIPTION

Figure 1:
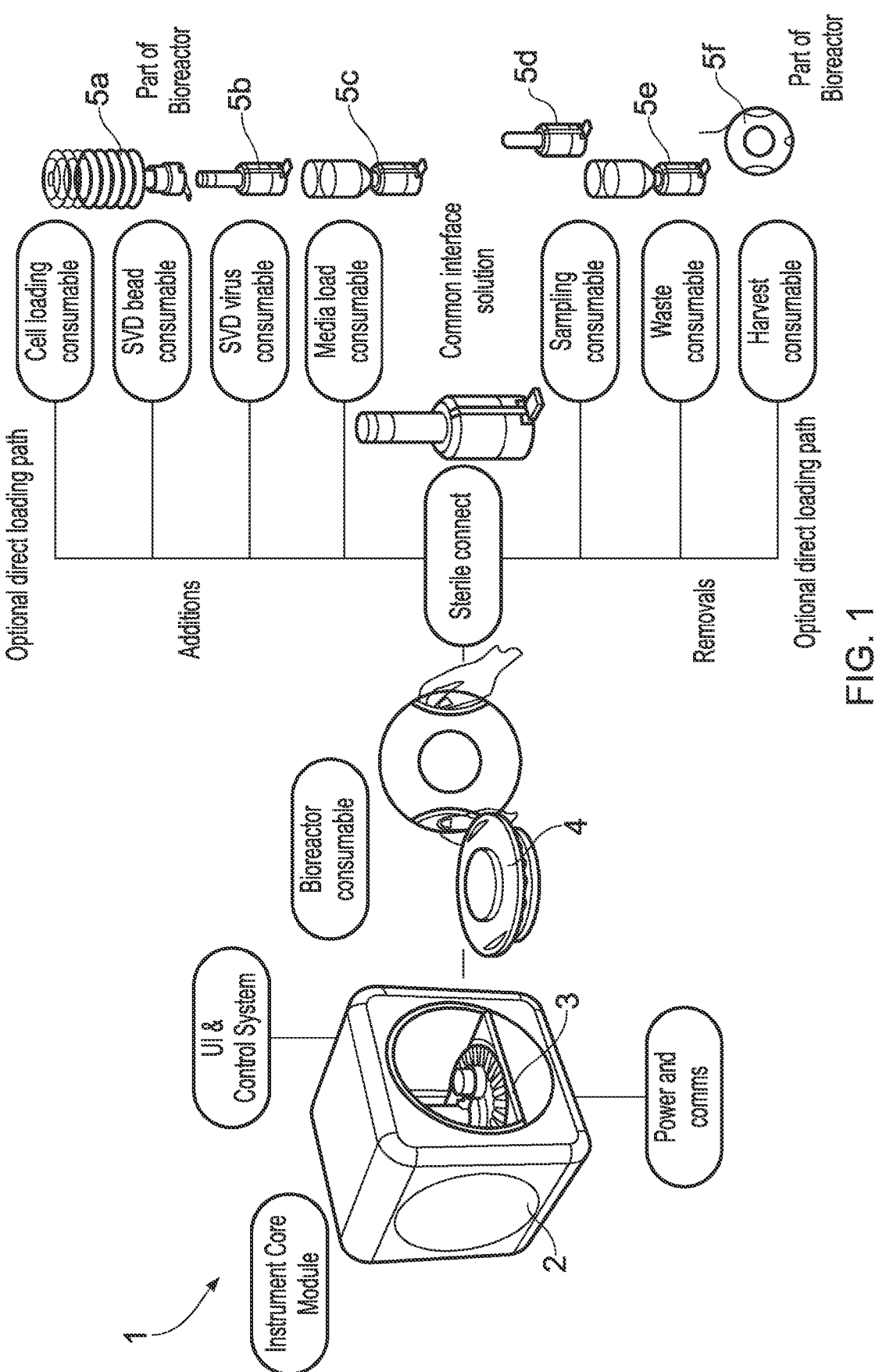
FIG. 1 shows a cell processing system that includes a bioreactor.

FIG. 1 shows a cell processing system 1 that includes a cell processing housing 2, a cell processing platform 3, a bioreactor 4, and various accessories, for example, "consumables" 5a-5f.

The cell processing housing 2 provides a closed environment for the cell processing platform 3 and is provided with power, connectivity and other utilities needed for the cell processing as described hereinafter. The cell processing platform 3 is adapted to receive the bioreactor 4 and support the bioreactor 4 within the cell processing housing 2. The cell processing platform 3 may include various components and systems that interact with the bioreactor 4 and/or the consumables 5a-5f. For example, the cell processing platform 3 may include an agitator that acts to agitate the bioreactor 4 so as to agitate a cell suspension provided within the bioreactor 4. In other examples, the cell processing platform 3 may include an accessory support arm adapted to hold one or more consumables 5a-5f. In examples, the cell processing platform 3 may include an actuator operable to actuate one or more the consumables 5a-5f. The cell processing platform 3 may be configured for automated operation of the cell processing system 1, or may permit manual operation.

The bioreactor 4, described in more detail with reference to FIG. 3, includes a container 12 and an interface plate 13. During use the container 12 holds a fluid in which the cell processing occurs. In particular, the fluid comprises a population of cells present in a liquid medium. The container 12 may be expandable, for example, by having a bellows wall. The bioreactor 4 is held in the cell processing housing 2 such that the container 12 can expand and retract as it is filled and emptied. The interface plate 13 may be engaged by the cell processing platform 3 and provides various functions relating to the bioreactor 4. For example, the interface plate 13 may have one or more connectors for transfer of fluids into and out of the container 12.

The consumables 5a-5f are for connecting to the bioreactor 4, optionally via the cell processing platform 3, in order to facilitate process steps of the cell culturing process.

In examples, a cell delivery consumable 5a is provided. The cell delivery consumable 5a is adapted to connect to the bioreactor 4 and deliver a cell suspension to the bioreactor 4. In particular, the cell delivery consumable 5a has a container that is filled with a cell suspension, and a connector that connects to the bioreactor 4 (optionally via the cell processing platform 3). The cell delivery consumable 5a is operable to transfer the cell suspension from the cell delivery consumable 5a into the bioreactor 4. The cell suspension may include "live" cells and a medium. Accordingly, the cell delivery consumable 5a delivers the cell suspension to a bioreactor 4.

The population of cells may comprise any cell type. Suitably the population of cells may comprise a homogenous population of cells. Alternatively, the population of cells may comprise a mixed population of cells.

The population of cells may comprise any human or animal cell type, for example: any type of adult stem cell or primary cell, T cells, CAR-T cells, monocytes, leukocytes, erythrocytes, NK cells, gamma delta t cells, tumor infiltrating t cells, mesenchymal stem cells, embryonic stem cells, induced pluripotent stem cells, adipose derived stem cells, Chinese hamster ovary cells, NS0 mouse myeloma cells, HELA cells, fibroblasts, HEK cells, insect cells, organoids, etc. Suitably the population of cells may comprise T-cells.

Alternatively, the population of cells may comprise any microorganism cell type, for example: bacterial, fungal, Archaean, protozoan, algal cells.

In examples, a fluid delivery consumable 5b is provided. The fluid delivery consumable 5b may hold a particle suspension, for example, a suspension of magnetic particles. The magnetic particles may be magnetic beads. The fluid delivery consumable 5b is operable to deliver the particle suspension to the bioreactor 4.

In examples, the fluid delivery consumable 5b may alternatively or additionally hold a virus suspension and deliver the virus suspension to the bioreactor 4.

In examples, a media delivery consumable 5c may be provided. The media delivery consumable 5c may comprise a container that is filled with one or more media, for example, a cell culturing medium, and a connector that connects to the bioreactor 4. The media delivery consumable 5c is operable to move the medium into the bioreactor. In examples, the media delivery consumable 5c is collapsible, similar to the cell delivery consumable 5a. The medium may be a liquid.

In examples, the liquid medium may be any sterile liquid capable of maintaining cells. The liquid medium may be selected from: saline or may be a cell culture medium. The liquid medium may be a cell culture medium selected from any suitable medium, for example: DMEM, XVIVO 15, TexMACS. The liquid medium may be appropriate for the type of cells present in the population. For example, the population of cells comprises T cells and the liquid medium comprises XVIVO 10.

In examples, the liquid medium may further comprise additives, for example: growth factors, nutrients, buffers, minerals, stimulants, stabilizers or the like.

In examples, the liquid medium comprises growth factors such as cytokines and/or chemokines. The growth factors may be appropriate for the type of cells present in the population and the desired process to be carried out. The liquid medium may comprise stimulants such as antigens or antibodies, which may be mounted on a support. Suitable stimulants are appropriate for the type of cells present in the population and the desired process to be carried out. When culturing T-cells, for example, antibodies are provided as a stimulant in the liquid medium. The antibodies may be mounted on an inert support such as beads, for example: dynabeads.

The additives may be present in the liquid medium at an effective concentration. An effective concentration can be determined by the skilled person on the basis of the population of cells and the desired process to be carried out using known teachings and techniques in the art.

In examples, the population of cells are seeded in the liquid medium at a concentration of between $1\times104$ cfu/ml up to $1\times108$ cfu/ml.

In examples, a sampling consumable 5d may be provided. The sampling consumable 5d may comprise a sampling vial. In examples, the sampling consumable 5d may comprise a vacutainer.

In examples, a waste consumable 5e may be provided. The waste consumable 5e may comprise a container, for example, an expandable container, adapted to receive a waste material removed from the bioreactor 4. The waste consumable 5e may include a filter arranged to filter the cells and/or other media from the fluid within the bioreactor so as only to extract the waste components.

In examples, a cell harvesting consumable 5f may be provided. The cell harvesting consumable 5f may comprise a container, for example, an expandable container, adapted to receive the cells (and optionally a cell medium) at or toward the end of the cell culturing process. The cell harvesting consumable 5f may include a filter arranged to filter a waste component from the cells and/or other media within the bioreactor so as only to extract the cells and desired media.

In examples, each of the consumables 5a-5f is connectable to the bioreactor 4 by a common connector. The connector may be that described in patent application PCT/GB2020/053229, as described further with reference to FIG. 5.

The connector can be connected to the consumable 5a-5f, or may be an integral part of the consumable 5a-5f. Operation of the connector, for example, by twisting or sliding, moves a needle so as to create a fluid connection between each end of the connector. Accordingly, the connector allows each consumable 5a-5f to be connected to the bioreactor 4, and then actuation of the connector forms a fluid connection between the consumable 5a-5f and the bioreactor 4 for transfer of materials as set out above. As explained further below, the connectors ensures sterility of the bioreactor 4 and the consumable 5 while creating a fluid connection between the two.

Figure 2:
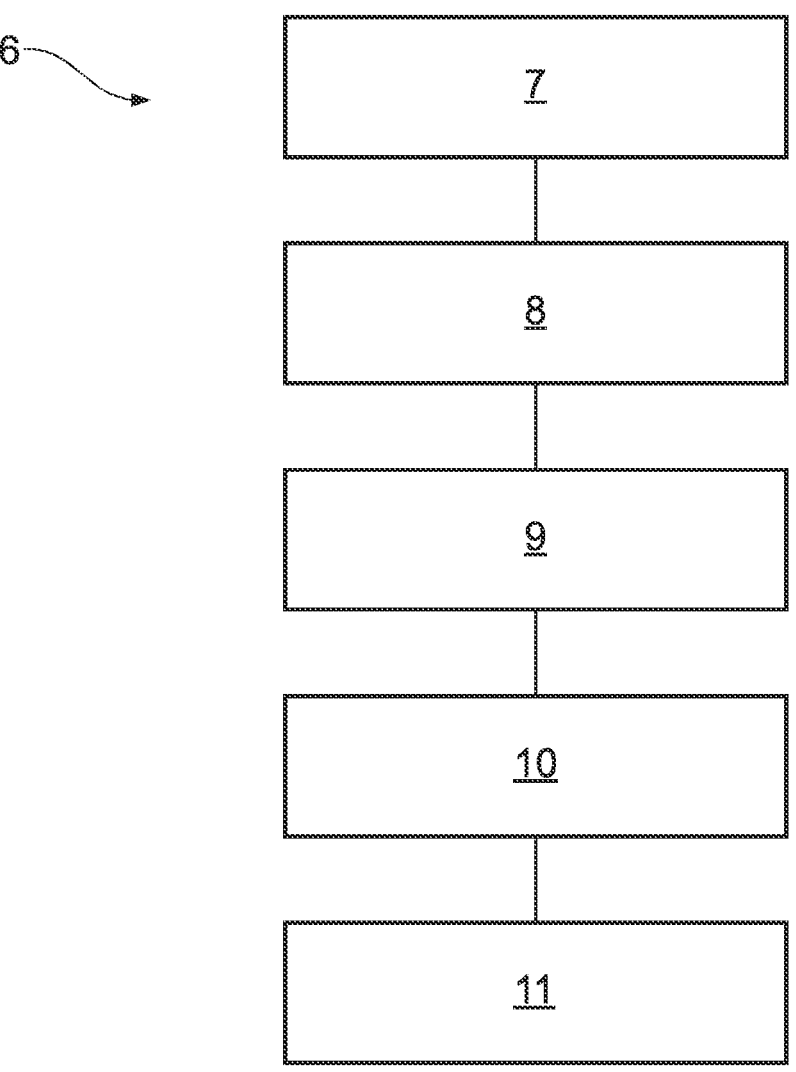
FIG. 2 schematically illustrates a cell culturing process.

FIG. 2 schematically illustrates a cell culturing process 6 based on the cell processing system 1 described with reference to FIG. 1. As shown in FIG. 2, initially the consumables 5a-5f are prepared at step 7. For example, a cell delivery consumable 5a may be filled with a cell suspension, and a bead loading consumable 5b may be filled with beads. A connector may be attached to the consumable 5a-5f before or after preparation. Preparation of the consumable(s) 5a-5f may include unpackaging the consumable(s) 5a-5f from a sterile package. It will be appreciated that only the consumables 5a-5f needed for the particular process, and the particular stage of the process, are prepared. For example, some processes would not use beads so a bead loading consumable 5b is not needed, and the cell harvesting consumable 5f is only needed at the end of the process 6.

Next, cells are loaded into the bioreactor 4 at step 8. In particular, a cell delivery consumable 5a is connected to the bioreactor 4 and operated to transfer a cell suspension from the cell delivery consumable 5a into the bioreactor 4. The cell delivery consumable 5a is connected to the bioreactor 4 via a connector, as described above, which forms a fluid connection between the cell delivery consumable 5a and the bioreactor 4.

Either before or after loading cells into the bioreactor 4 (step 8), the bioreactor 4 is loaded into the cell processing housing 2 at step 9. In some examples, the bioreactor 4 is attached to the cell processing platform 3 within the cell processing housing 2.

Within the cell processing housing 2 the cells are processed, at step 10, in the bioreactor 4. During processing (step 10) the pressure, temperature, pH and other environmental characteristics within the bioreactor 4 are controlled to ensure that conditions enable cell processing. Cell processing (step 10) may comprise reprogramming the cells, for example, by using CAR-coding viral DNA. Cell processing (step 10) may comprise cell culturing.

During cell processing (step 10) additional consumables 5a-5f may be used to add materials to the bioreactor 4, to extract a sample from the bioreactor 4, and/or to extract waste from the bioreactor 4. For example, a delivery consumable 5b may be used to add magnetic beads to the bioreactor. In examples, a delivery consumable 5b may be used to add a virus suspension or solution to the bioreactor (e.g., CAR-coding viral DNA). In examples, a media loading consumable 5c may be used to add one or more media to the bioreactor 4. For example, a media loading consumable 5c may be used to add a balanced salt solution or a basal media to the bioreactor 4. In examples, a sampling consumable 5d may be used to extract a sample from the bioreactor for testing. In examples, during or after cell processing (step 10) a waste consumable 5e may be used to extract a waste media from the bioreactor 4.

After cell processing (step 10) the cells are harvested at step 11. Cell harvesting (step 11) may initially use a waste consumable 5e to extract a waste component. A harvesting consumable 5*f* can be attached to bioreactor 4 to receive the cells from the bioreactor 4. The cells may be harvested in a media, for example, a cell suspension may be harvested.

As shown in FIG. 3, the bioreactor 4 comprises a container 12 and an interface plate 13. The interface plate 13 comprises at least one connector interface 21 for connecting to an external component, for example, one of the consumables 5*a*-5*f* described above. In examples, the connector interface 21 includes a septum seal that maintains a sealed environment within the container 12 and also permits a needle to pass through to create a fluid connection into the container 12.

The container 12 is a collapsible container. In particular, the container 12 has a bottom wall 15 disposed opposite to the interface plate 13, and a collapsible wall 16 defining a sidewall of the container 12. A top part 17 of the collapsible wall 16 is attached to the interface plate 13. The top part 17 may include a rigid ring or similar for attaching to the interface plate 13. The collapsible wall 16 is collapsible such that the bottom wall 15 can move toward and away from the interface plate 13, changing the internal volume of the container 12.

The collapsible wall 23 may be a bellows wall, having a concertina arrangement that allows the collapsible wall 23 to fold onto itself in order to collapse. In particular, the collapsible wall 23 may comprise a series of alternately arranged inward folds 16*a* and outward folds 16*b* that allow the collapsible wall 23 to collapse like a bellows or concertina. The inward folds 16*a* and outward folds 16*b* may be formed by thinned sections in the collapsible wall 23, with the inward folds 16*a* comprise a thinned section arranged on the outer surface of the collapsible wall 23, and the outward folds 16*b* comprising a thinned section arranged on the inner surface of the collapsible wall 23.

The container 12 can therefore expand and contract, or be expanded and contracted, according to the material held in the container 12. In particular, the collapsible container 12 may expand as the cell culture within the container 12 grows, and/or as additional materials are added. The cell processing housing (2, see FIG. 1) may comprise an actuator adapted to move, for example, push and/or pull, the bottom wall 15 of the container 12 and/or the interface plate 13 to change the volume of the container 12.

As illustrated, the interface plate 13 also includes an expansion container 14, otherwise called a breathing container. The expansion container 14 allows for the container 12 to expand and contract without greatly changing the pressure in the container 12. Alternatively or additionally, the expansion container 14 may be operable, for example, by being mechanically or manually compressed or expanded, to expand or retract the collapsible wall 16 of the container 12 and thereby change a volume of the container 12. Alternatively or additionally, the expansion container 14 may be operable, for example, by being mechanically or manually compressed or expanded, to alter the pressure within the container 12.

FIGS. 4A and 4B illustrate an example of connecting a fluid delivery consumable 5*b* to the bioreactor 4 of FIG. 3. As shown, the fluid delivery consumable 5*b* has a vial 22 and a connector 19. The vial 22 holds a fluid, for example, a particle suspension or a virus suspension, and a plunger portion 23 is provided to urge the fluid out of the vial 22 toward the connector 19. The plunger portion 23, described further hereinafter, has a plunger that moves into the vial 22.

As shown in FIG. 4B, the connector 19 is connected to the interface plate 13 of the bioreactor 4, in particular, to a connector interface 21 of the interface plate 13. In examples, the connector interface 21 comprises a seal, for example, a septum seal, that seals the bioreactor 4. The connector 19 is actuatable, as described with reference to FIG. 5, to form a fluid connection between the vial 22 of the fluid delivery consumable 5*b* and the container 12 of the bioreactor 4. In examples, the connector 19 comprises a needle that is moved when the connector 19 is actuated in order to pierce the seal of the connector interface 21 and form a fluid connection with the bioreactor.

Once the fluid connection is established the fluid (i.e., the beads and/or virus suspension) provided in the vial 22 of the fluid delivery consumable 5*b* is transferred from the vial 22 to the container 12 of the bioreactor 4. The plunger portion 23 of the fluid delivery consumable 5*b* may be actuated, in particular, depressed, either manually by an operator or by an actuator of the cell processing system (1, see FIG. 1). Depressing the plunger portion 23 of the fluid delivery consumable 5*b* urges the fluid through the fluid connection and into the container 12 of the bioreactor 4.

Once the fluid has been transferred from the fluid delivery consumable 5*b* to the bioreactor 4 the fluid delivery consumable 5*b* can be detached from the bioreactor 4. On detaching the connector 19 from the connector interface 21 the seal of the connector interface 21 may reseal the connector interface 21. For example, the seal of the connector interface 21 may be a septum seal that reseals on withdrawal of the needle.

Figure 5:
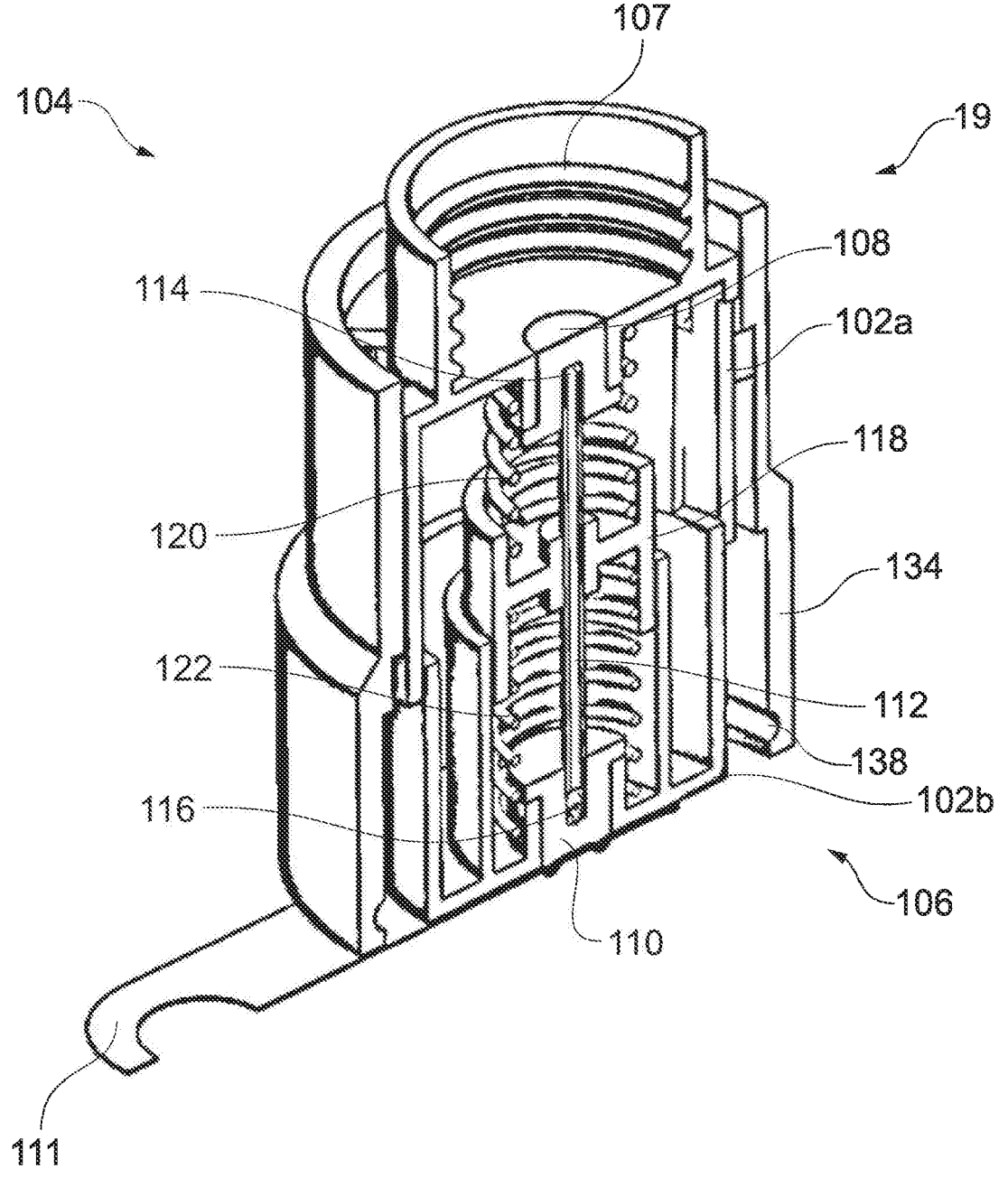
FIG. 5 shows an example connector for connecting the fluid delivery consumable to the bioreactor.

FIG. 5 illustrates the connector 19. The connector 19 is used to attach a consumable 5*a*-5*f* to the bioreactor 4, in particular, to the connector interface 21 of the interface plate 13 of the bioreactor 4. The connector 19 may be as described in patent application PCT/GB2020/053229.

In particular, as shown in FIG. 5 the connector 19 comprises a housing 102 having an upper housing portion 102*a* and a lower housing portion 102*b*. The housing 102 extends along a longitudinal axis between a distal end 104 and a proximal end 106. The upper housing portion 102*a* may be axially moveable, or slidable, with respect to the lower housing portion 102*b*, as will be described further below.

The housing 102 includes a threaded portion 107 at its distal end 104 for connecting to a corresponding threaded portion of the vial (22, see FIG. 4A) of the delivery consumable (5*b*, see FIG. 4A). The threaded portion 107 is formed on the upper housing portion 102*a*. As will be clear to the skilled person, the housing 102 may be provided without the threaded portion 107, and instead be provided with another suitable connection mechanism for connecting to a portion of the vial (22, see FIG. 4A).

The connector 19 also includes a connector portion at its proximal end 106 for connecting to the bioreactor (4, see FIG. 3), in particular, a connector interface (21, see FIG. 4B) of the bioreactor 4. The connector portion may be a groove 138, as illustrated in FIG. 5, configured to receive one or more protrusions or legs on the bioreactor. Alternatively, the connector 19 may comprise a threaded portion or other connector portion for connecting to the bioreactor.

In this embodiment, the connector 19 includes a first septum seal 108 disposed at the distal end 104 of the housing 102, and a second septum seal 110 disposed at the proximal end 106 of the housing 102. The first septum seal 108 includes a substantially planar, i.e., flat, pierceable surface facing outwardly at the distal end 104. The second septum seal 110 includes a generally annular portion, extending outwardly at the proximal end 106, enclosing a substantially planar, i.e., flat, pierceable surface facing outwardly at the proximal end 106. The housing 102 further includes a hollow needle 112 that is biasedly mounted within the housing 102. The hollow needle 112 is generally coaxially aligned with the longitudinal axis. The hollow needle 112 includes a first end 114, facing the first septum seal 108, and a second end 116, facing the second septum seal 110. The first end 114 is configured to be able to pierce the first septum seal 108, in use, and the second end 116 is configured to be able to pierce the second septum seal 110, in use. The first septum seal 108, the second septum seal 110, or both the first and second septum seal 108, 110 may optionally be provided with a removable aseptic paper seal 111.

The hollow needle 112 is mounted within the housing 102 through a collar 118 that is spring-biased by a first helical spring 120 and a second helical spring 122. In other embodiments, the hollow needle 112 may be mounted in another suitable manner, for example, the hollow needle 112 may be statically mounted, i.e., such that it does not move, and the housing 102 may be moveable about the hollow needle 112. The first spring 120 acts between the distal end 104 of the housing 102 and the collar 118. The second spring 122 acts between the proximal end 106 of the housing 102 and the collar 118. In this way, the first spring 120 provides a first biasing force to the hollow needle 112, via the collar 118, in a direction toward the proximal end 106 of the housing 102, and the second spring 122 provides a second biasing force to the hollow needle 112, via the collar 118, in a direction toward the distal end 104 of the housing 102.

The connector 19 further includes an actuating mechanism for causing the hollow needle 112 to pierce the septum seals 108, 110. By piercing the first and second septum seals 108, 110 the hollow needle 112 creates a fluid path between the distal end 104 and the proximal end 106 of the connector 19, and so during use creates a fluid connection between the vial 22 of the delivery consumable 5b and the container 12 of the bioreactor 4, as shown in FIG. 4B.

In the example illustrated in FIG. 5 the actuating mechanism includes an outer sleeve 134 that is arranged to collapse the upper housing portion 102a with respect to the lower housing portion 102b. The outer sleeve 134 is rotatable with respect to the housing 102 about the central longitudinal axis of the housing 102. For example, one of the outer sleeve 134 and the housing 102 may include a helical groove, and the other of the outer sleeve 134 and housing 102 may include a protrusion that engages the groove such that when the upper housing portion 102a collapses with respect to the lower housing portion 102b the outer sleeve 134 is rotated.

When the connector 19 is attached to the vial (22, see FIG. 4A), in particular, via the threaded portion 107, the first septum seal 108 seals the end of the vial (22, see FIG. 4A). The proximal end 106 of the connector 19 is then attached to the connector interface (21, see FIG. 4B), for example, by a clipping mechanism, a sliding mechanism, a threaded connection, or clamping. In this position, actuation of the actuating mechanism, in particular, rotation of the outer sleeve 134, causes the upper housing portion 102a to collapse with respect to the lower housing portion 102b and the hollow needle 112 pierces the first septum seal 108 and the second septum seal 110 and creates a fluid connection through the connector 19, between the vial (22, see FIG. 4A) and the bioreactor (4, see FIG. 4B).

Accordingly, the connector 19 initially provides a sealing closure for the vial (22, see FIG. 4A), and the fluid connection is formed entirely within the connector 19, which advantageously maintains a sterile environment.

Once the fluid has been transferred to the bioreactor (4, see FIG. 4B) through the hollow needle 112, the actuation mechanism can be reversed so that the needle withdraws from the first septum seal 108 and optionally also the second septum seal 110. The first and/or second septum seal 108, 110 reseal on withdrawal of the hollow needle 112. The connector 19, and the vial (22, see FIG. 4A), can then be detached from the bioreactor (4, see FIG. 4B).

In examples, an end of the vial 22 of the delivery consumable 5b illustrated in FIG. 4A comprises a plug seal, for example, a septum seal, so that the vial 22 is sealed before the connector is connected. The plug seal of the vial 22 can be pierced by the hollow needle 112.

In examples, the connector interface 21 of the bioreactor 4 illustrated in FIGS. 3 and 4B comprises a further septum seal that is pierced by the hollow needle 112 in use. Accordingly, when the connector 19 is detached the bioreactor 4 remains sealed.

Figure 6:
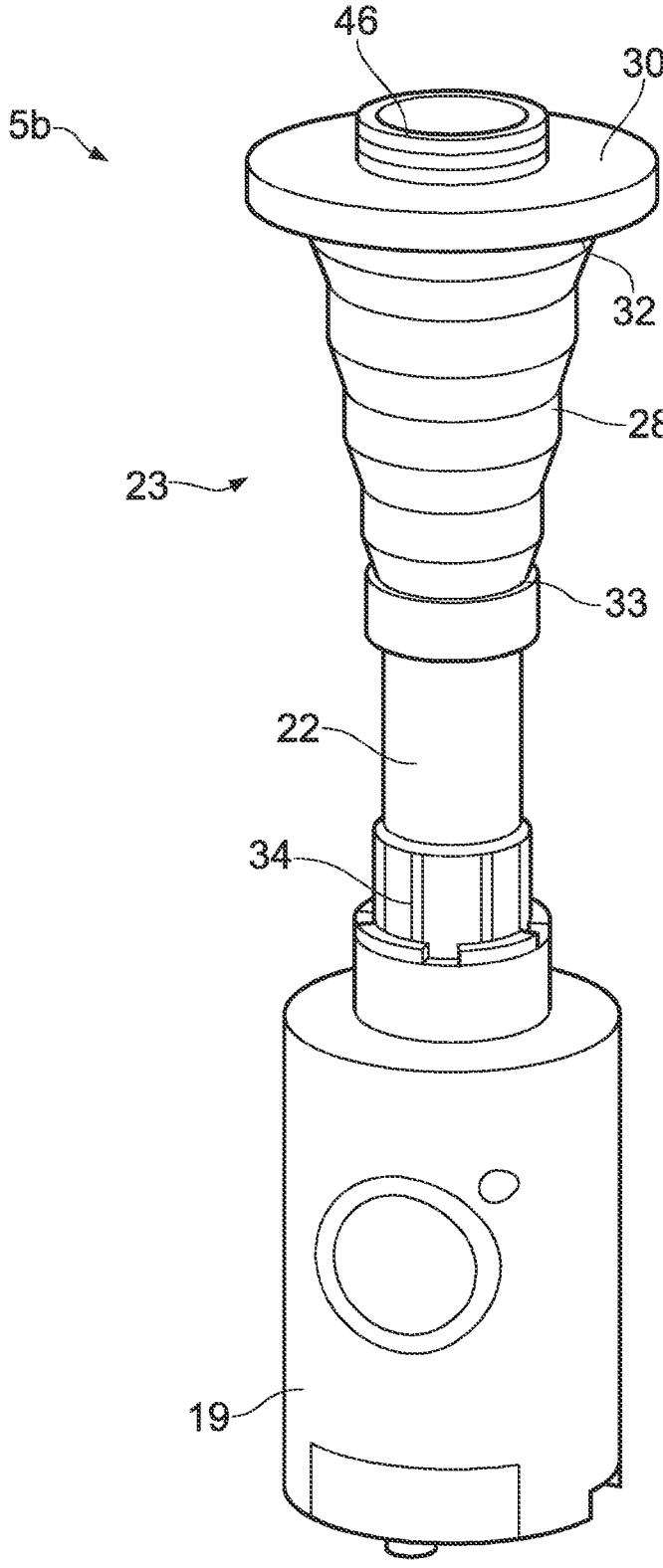
FIG. 6 shows an example fluid delivery consumable.
Figure 7:
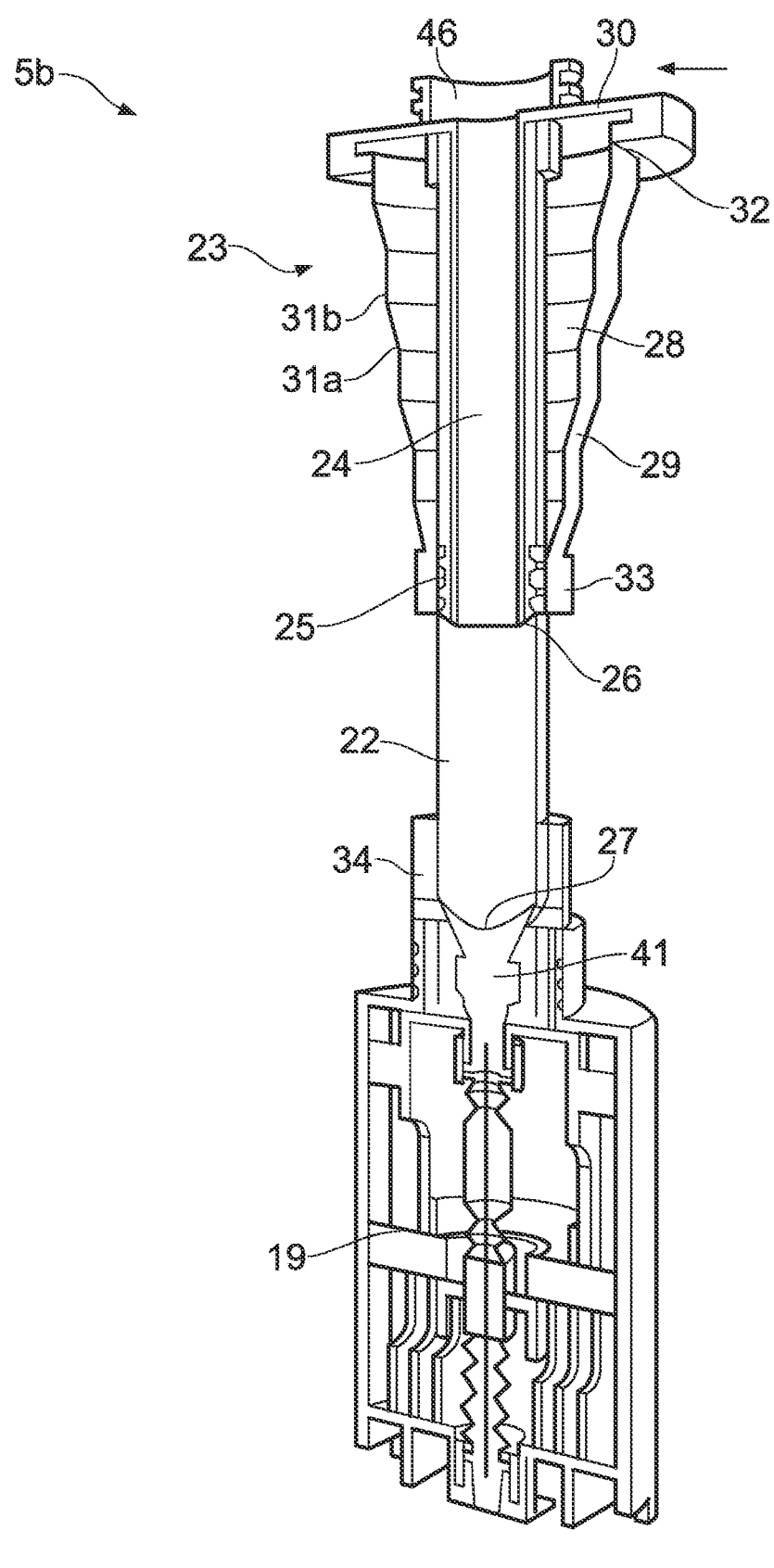
FIG. 7 shows a cross-section of the fluid delivery consumable of FIG. 6.
Figure 8:
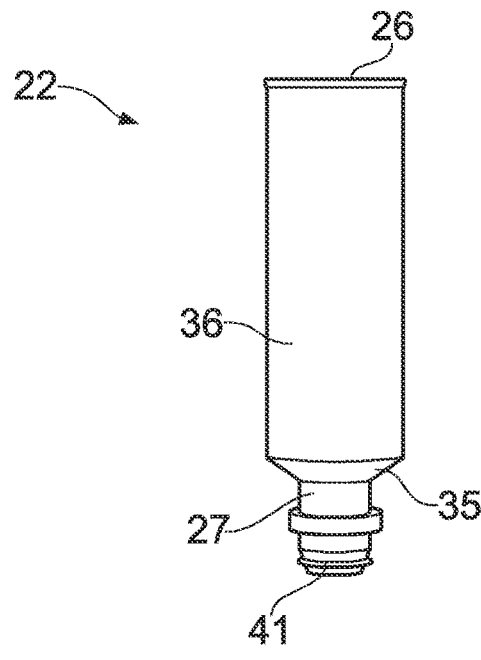
FIG. 8 shows the vial of the fluid delivery consumable of FIG. 6.

FIG. 6 illustrates a fluid delivery consumable 5b for delivering a fluid dose to the bioreactor (4, see FIG. 4B), and FIG. 7 illustrates a cross-section of the fluid delivery consumable 5b. In particular, the fluid delivery consumable 5b delivers a suspension of beads such as magnetic beads, or a virus suspension. As illustrated, the fluid delivery consumable 5b has a vial 22 in which the fluid dose is held, and a connector 19 that is connectable to the bioreactor (4, see FIG. 4B). In particular, as shown in FIG. 4B the connector 19 is connectable to the connector interface 21 of the bioreactor 4. The fluid delivery consumable 5b also includes a plunger portion 23 that is operable to urge the fluid does out of the vial 22, through the connector 19, and into the bioreactor (4, see FIG. 4B). FIG. 8 shows the vial 22 in isolation, and FIG. 9 shows the vial 22 and plunger 24.

Figure 9:
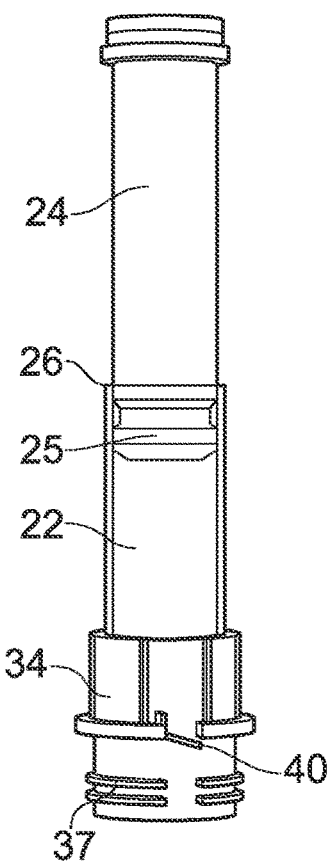
FIG. 9 shows the vial, plunger, and collar of the fluid delivery consumable of FIG. 6.

As shown in FIGS. 7, 8 and 9, the vial 22 includes an open end 26 and an outlet 27 opposite to the open end 26. The vial 22 has a tubular portion 36 that is substantially straight, and a funnel portion 35 that narrows to the outlet 27.

The plunger portion 23 comprises a plunger 24 arranged to pass into the open end 26 of the vial 22 and move into the vial 22 in a direction toward the outlet 27. The plunger 24 includes a piston having a seal 25 that seals against an inner surface of the vial 22, in particular, against the inner surface of the tubular portion 36, to provide a substantially fluid-tight seal. The seal 25 may be in the form of a piston attached to the plunger 24, or the piston may be formed as a part of the plunger 24. The seal 25 on the plunger 24 or piston may include one or more O-rings. Accordingly, from the position shown in FIGS. 6, 7 and 9 the plunger 24 can be depressed to urge the fluid toward the outlet 27.

As shown in FIGS. 6 and 7, the plunger portion 23 also includes a gaiter 28. The gaiter 28 is formed by a collapsible wall 29, for example, a bellows wall. The gaiter 28 also includes a cap 30 attached to an end of the plunger 24. The collapsible wall 29 extends between the cap 30 and the open end 26 of the vial 22. The collapsible wall 29 may be attached to the open end 26 of the vial 22 by adhesive, or by clamping or other attachment mechanism. A clamping ring may be provided to clamp the end of the collapsible wall 29 to the vial 22. The collapsible wall 29 may be attached to the cap 30 by adhesive, or by clamping or other attachment mechanism. A clamping ring may be provided to clamp the end of the collapsible wall 29 to the cap 30.

The collapsible wall 29 is formed by an alternating series of inward folds 31a and outward folds 31b that permit sections of the collapsible wall 29 to fold against each other. The gaiter 28, in particular, the collapsible wall 29, surrounds the plunger 24 when it is outside of the vial 22, and therefore provides a sealed environment for the plunger 24. As will become clear, the plunger 24 may be moved from within the vial 22 to outside of the vial 22 to fill the fluid delivery consumable 5b, and then depressed back into the vial 22 to deliver the fluid to the bioreactor 4, and therefore the gaiter 28 can prevent contamination of the plunger 24 and maintain the sterility of the vial 22.

As illustrated, a first end 32 of the collapsible wall 29 that attaches to the cap 30 is larger than a second end 33 of the collapsible wall 29 that attaches to the vial 22. In this way, the collapsible wall 29 collapses inwards when collapsed.

The gaiter 28, in particular, the cap 30 and collapsible wall 29, provide a sealed enclosure for the plunger 24. As will become clear, the plunger 24 may be moved from within the vial 22 to outside of the vial 22 to fill the fluid delivery consumable 5b, and then depressed back into the vial 22 to deliver the fluid to the bioreactor 4, and therefore the gaiter 28 can prevent contamination of the plunger 24 and maintain the sterility of the vial 22.

In examples, the cap 30 may comprise an engaging feature 46 that is engageable by another part of the cell processing system (1, see FIG. 1), in particular, an actuator in the cell processing housing (2, see FIG. 1). The actuator may engage the engaging feature 46, for example, to depress or retract the plunger 24.

The connector 19, described with reference to FIG. 5, may be attached to the vial 22, for example, via a threaded connection (see threaded portion 107 in FIG. 5). In particular, the end of the vial 22 where the outlet 27 is formed may have an external thread to engage an internal thread on the connector 19 to provide direct connection between the vial 22 and the connector 19.

In other examples, as illustrated in FIGS. 6, 7 and 9, the connector 19 may be attached to the vial 22 via a collar 34. The collar 34 surrounds an end of the vial 22, including the funnel portion 35 and the outlet 27. The collar 34 is attached to the vial 22 by a push fit. The collar 34 may include an O-ring or other elastomeric member to increase the holding force of the push fit. Alternatively, the collar 34 may be attached to the vial 22 by adhesive. The collar 34 includes a threaded portion, in particular, an external thread 37, for connecting to a thread of the connector 19. However, it will be appreciated that other connection mechanisms may be provided between the collar 34 and the connector 19. For example, a bayonet connecting mechanism may be provided between the collar 34 and the connector 19.

In one example, shown in FIG. 10, the collar 34 is attached to the vial 22, in particular, the end of the vial 22 with the outlet 27, using a lock ring 42. The lock ring 42 comprises a ring portion 43 and a plurality of tangs 44 extending from the ring portion 43 and arranged to wedge between the vial 22 and the collar 34 so as to secure the collar 34 to the vial 22. The tangs 44 may be shaped to clip over an edge formed on the vial 22 and/or on the collar 34. The vial 22, in particular, the funnel portion 35, may have one or more recesses or grooves that are engaged by the tangs 44.

As shown in FIGS. 9 and 10, the collar 34 also includes a clip member 40 extending from the collar 34 in an angled anti-clockwise direction. The collar 34 may include more than one clip member 40, for example, two or three clip members 40. The clip members 40 are resiliently deformable to flex about the point where the clip member 40 extends from the collar 34. The clip member 40 is arranged to engage a recess on the connector 19 when the collar 34 is screwed onto the connector 19. In particular, the free end of the clip member 40 is arranged to be received in the recess on the connector 19. The clip member 40 engages the recess on the connector 19 when the thread 37 of the collar 34 is screwed into the thread of the connector 19. Accordingly, the clip member 40 prevents the collar 34 from being unscrewed from the connector 19 so that once the connector 19 is attached to the collar 34 and vial 22 it cannot be removed.

As shown in FIG. 10, the collar 34 may include a scale 45 arranged to overlay a part of the vial 22 and provide gradation marks indicating the volume of fluid in the vial 22.

The connector 19 is connectable to the bioreactor (4, see FIG. 3), in particular, to the connector interface (21, see FIG. 3) of the bioreactor 4, as previously described. As described with reference to FIG. 5, after the connector 19 has been attached to the bioreactor 4 it can be actuated to create a fluid connection between the delivery consumable 5b and the bioreactor 4. After the fluid connection is formed by the connector 19 the plunger 24 can be depressed to urge the fluid into the bioreactor 4.

As shown, the collar 34 covers the outlet 27 end of the vial 22, and the gaiter 28 covers the open end 26 of the vial 22. Accordingly, the vial 22 is protected against damage by dropping as there are no exposed edges of the vial 22.

In examples, the connector 19 has a seal, for example, the first septum seal 108 shown in FIG. 5, that covers or plugs the outlet 27 of the vial 22. As described with reference to FIG. 5, the first septum seal 108 can be pierced by the hollow needle 112 during use.

Additionally or alternatively, the vial 22 may comprise an openable valve, a breakable seal, or other sealing mechanism that initially seals the vial 22. Such a seal may be openable or pierceable once the connector 19 is connected to the bioreactor to provide a fluid connection between the delivery consumable 5b and the bioreactor. In particular, as shown in FIGS. 7 and 8 the vial 22 may include a plug seal 41 to seal the outlet 27. The plug seal 41 may be pierceable by the hollow needle 112 of the connector 19 during use. The plug seal 41 may be a septum seal. The plug seal 41 provides a sealed vial 22 when the connector 19 is not attached.

When the connector 19 is actuated the hollow needle 112 of the connector 19, shown in FIG. 5, pierces the plug seal 41 and any additional seal on the connector 19 (e.g., the seal 108) to create a fluid connection with the vial 22. The other end of the hollow needle 112 creates a fluid connection with the bioreactor (4, see FIG. 4B), as previously described. Accordingly, once the connector 19 has been actuated the plunger 24 can be depressed to move the fluid from the vial 22 into the bioreactor.

Figure 11:
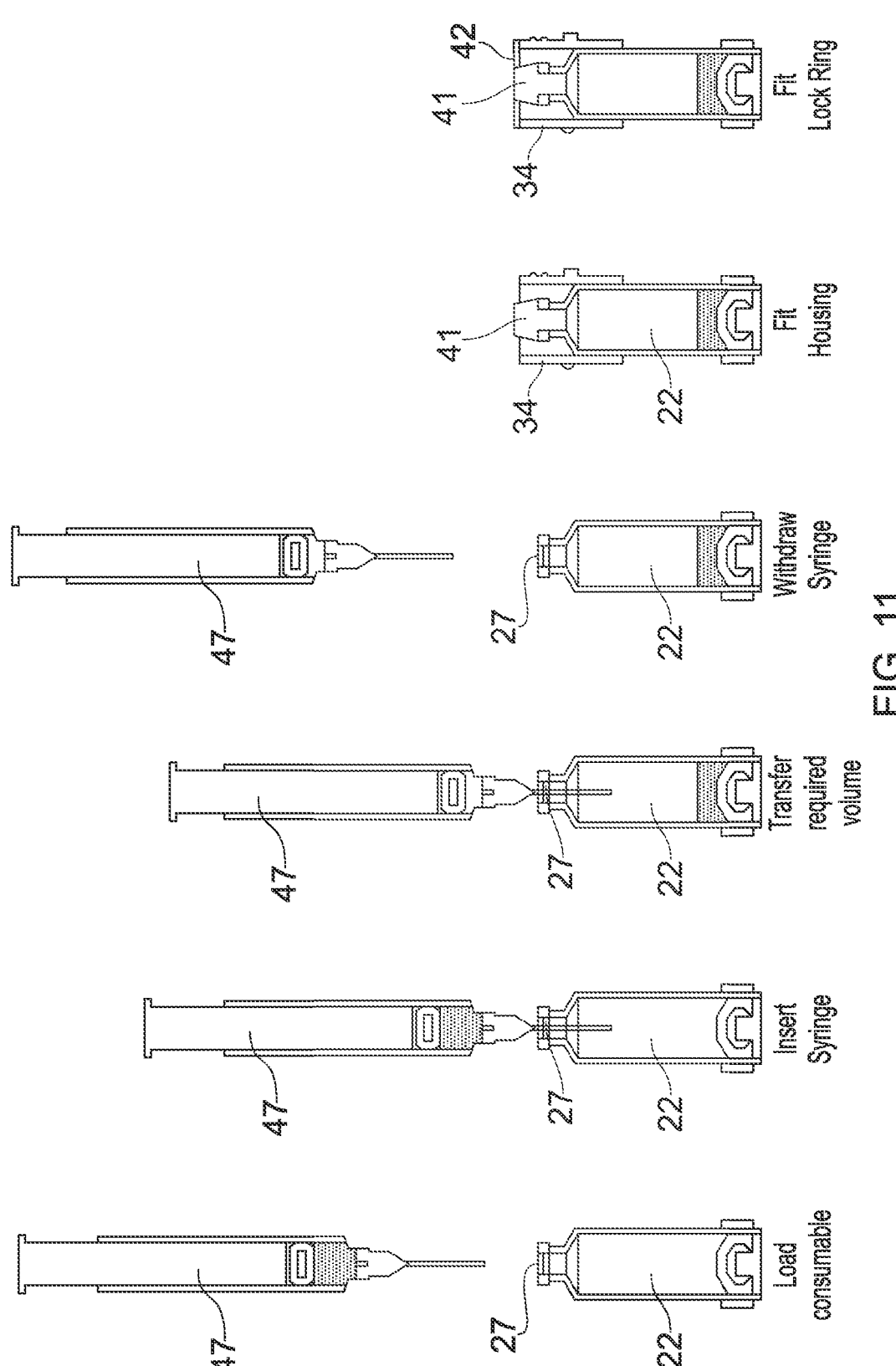
FIG. 11 shows an example process of filling the fluid delivery consumable.
Figure 12:
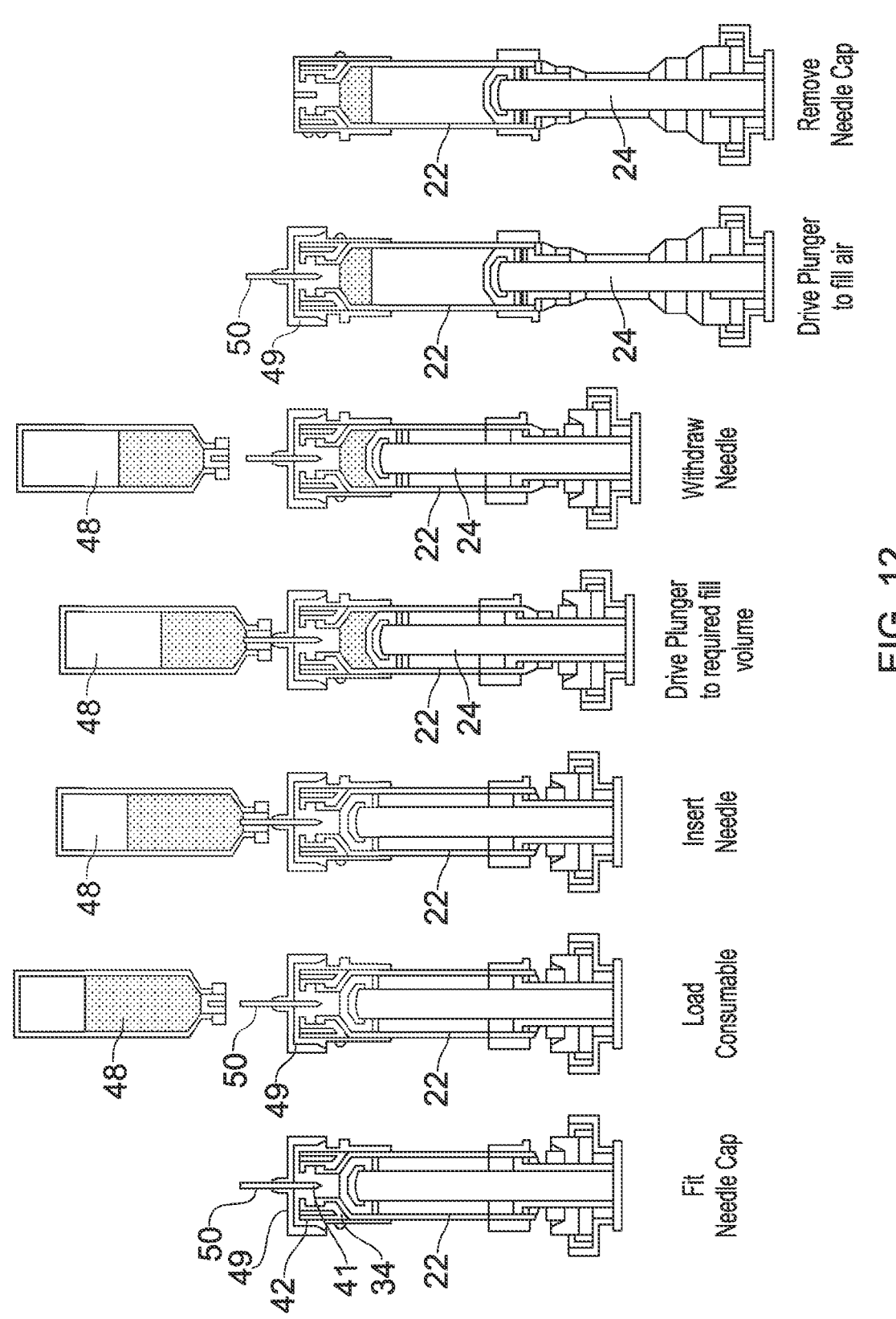
FIG. 12 shows another example process of filling the fluid delivery consumable.
Figure 13:
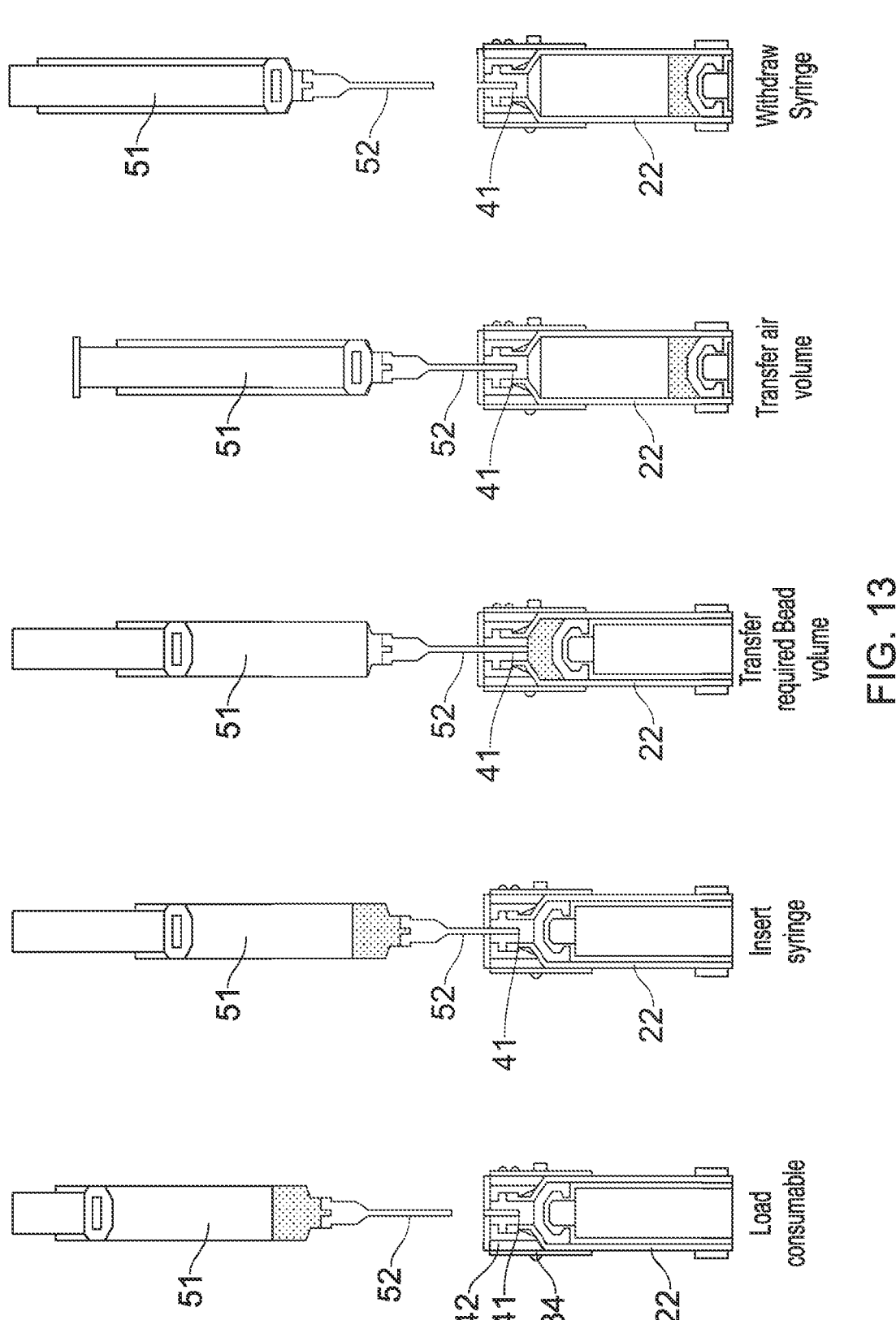
FIG. 13 shows another example process of filling the fluid delivery consumable.

FIGS. 11 to 13 illustrate options for filling the delivery consumable 5b, in particular, the vial 22, with fluid.

In the example of FIG. 11, the vial 22, without the collar 34 or plug seal 41, is inverted and filled with fluid through the outlet 27. A syringe 47 is used to add the fluid to the vial 22. Once the fluid is provided in the vial 22 the plug seal 41 and collar 34 are attached to the outlet 27 of the vial 22 using the lock ring 42 to secure the collar 34 and plug seal 41 to the vial 22. An amount of air is also captured in the vial 22 at this point. The air is used to purge the fluid delivery consumable 5, in particular, the vial 22 and hollow needle 112, during use. The connector 19 can then be screwed onto the collar 34, as previously described.

In the example of FIG. 12, the vial 22 is provided with the plug seal 41 and collar 34 in place, attached to the end of the vial 22 using the lock ring 42. In this example, the plug seal 41 is a septum seal that reseals after being pierced by a needle. A needle cap 49 is then attached to the vial 22, over the collar 34. The needle cap 49 includes a needle 50 that pierces the plug seal 41 and forms a fluid connection into the vial 22. As illustrated, the needle 50 also extends the other way and can be inserted into a supply vial 48 containing the fluid. The plunger 24 can be withdrawn to draw fluid from the supply vial 48 into the vial 22. The supply vial 48 can then be removed, and the plunger 24 withdrawn further to draw air into the vial 22. The needle cap 49 can then be removed and the plug seal 41 will reseal. The air is used to purge the fluid delivery consumable 5, in particular, the vial 22 and hollow needle 112, during use.

In the example of FIG. 13, the vial 22 is provided with the plug seal 41 and the collar 34 attached to the vial 22 by the lock ring 42. In this example the plug seal 41 is a septum seal that reseals after being pierced by a needle. A syringe 51 with a needle 52 is used to pierce the plug seal 41 and transfer the fluid and some air into the vial 22. The plunger 24 may be displaced by the pressure of the fluid, or by manually retracting it. When the needle 52 is removed the septum seal of the plug seal 41 reseals the vial 22.

In the examples of FIGS. 11 to 13 the vial 22 may be filled with the fluid in a protective environment, for example, in an extractor chamber such as a Class A MSC hood.

Once the vial 22 has been provided with the fluid the connector 19 is attached, as previously described. The fluid delivery consumable 5b with the connector 19 can be stored and transported in this state. Before connecting to the bioreactor (4, see FIG. 4B) the fluid may be mixed by loading the fluid delivery consumable 5b into an agitator, such as a vortex mixer, that shakes, rolls and/or rotates the delivery consumable 5b to mix the fluid. This is advantageous if the fluid is a suspension, in order to re-suspend the fluid constituents.

FIGS. 14A to 14D illustrate actuation of the fluid delivery consumable 5b after the fluid delivery consumable 5b has been connected to the bioreactor (4, see FIG. 4B) via the connector 19 as shown in FIG. 4B.

Figures 14A, 14B:
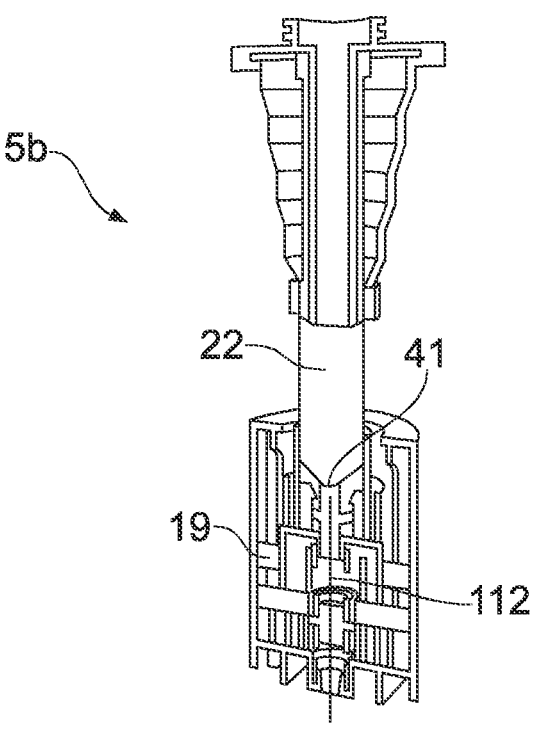
FIGS. 14A to 14D illustrate operation of the fluid delivery consumable to deliver a fluid to the bioreactor.

As shown in FIG. 14A, once connected the connector 19 is actuated as described with reference to FIG. 5 so that the hollow needle 112 forms a fluid connection between the vial 22 and the bioreactor (4, see FIG. 4B). In particular, the hollow needle 112 pierces the plug seal 41 on the vial 22 and any seal on the bioreactor. The hollow needle 112 also moves into engagement with the bioreactor (4, see FIG. 4B) so that a fluid connection is provided between the vial 22 and the bioreactor (4, see FIG. 4B).

As shown in FIG. 14B, the plunger 24 is then depressed to urge the fluid through the hollow needle 112 and into the bioreactor (4, see FIG. 4B). As the plunger 24 is depressed the gaiter 28, in particular, the collapsible wall 29, collapses and folds up. The plunger 24 may be depressed manually or may be depressed by an actuator on the cell processing housing (2, see FIG. 1).

Referring to FIGS. 14B and 4B, when depressing the plunger 24 to deliver the fluid to the bioreactor 4, the base 15 of the bioreactor may be raised toward the interface plate 13 to reduce the distance between the vial 22 and the base 15 of the bioreactor 4. This may reduce impact on the fluid caused by falling through the bioreactor 4.

Figure 14C:
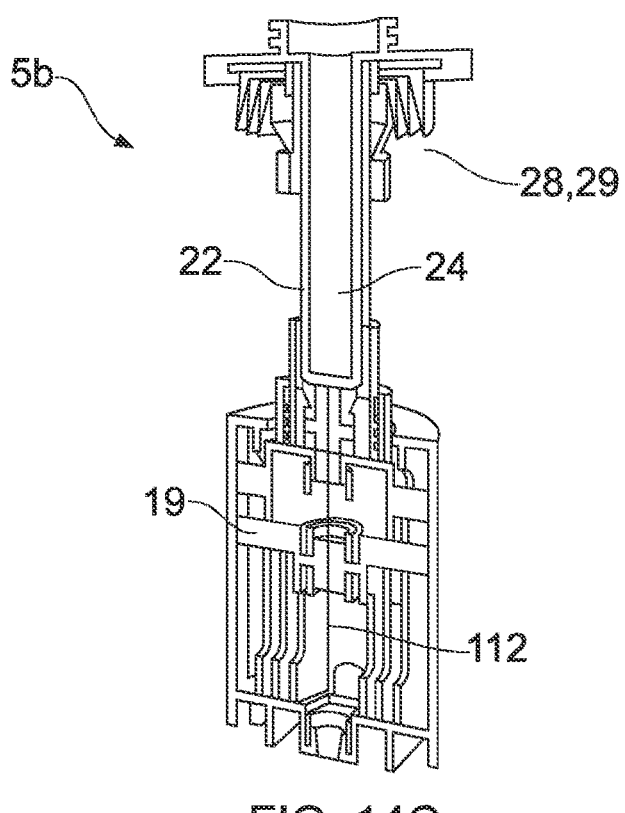
Figure 14D:
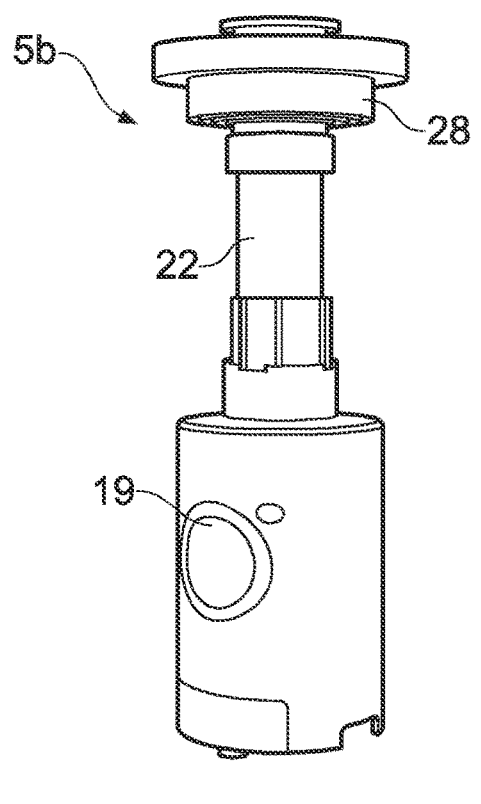

As shown in FIGS. 14C and 14D, once the fluid has been delivered to the bioreactor (4, see FIG. 4B) the connector 19 can be disengaged so that the hollow needle 112 withdraws from the bioreactor (4, see FIG. 4B). The bioreactor (4, see FIG. 4B) may include a septum seal that reseals after withdrawal of the hollow needle 112. The connector 19 is then disconnected from the bioreactor (4, see FIG. 4B) and the fluid delivery consumable 5b can be disposed of. As explained above, in some examples the connector 19 cannot be disconnected from the vial 22 after use due to the clip member(s) 40. Accordingly, the fluid delivery consumable 5b, including the connector 19 cannot be reused.

In examples, the fluid delivered to the bioreactor 4 by the fluid delivery consumable 5b comprises a plurality of magnetic particles. The magnetic particles may be magnetic beads. The magnetic particles may comprise iron oxides, such as magnetite (Fe3O4), which give them superparamagnetic properties. The magnetic particles may be provided with surface coatings and chemistries that bind to nucleic acids, proteins, or other biomolecules within the bioreactor 4. The magnetic particles can be separated from the fluid by creating a magnetic field to attract the magnetic particles and therefore the particles bonded thereto. The magnetic particles may be used for a separation process to separate components, in particular, nucleic acids, proteins, or other biomolecules, of the fluid in the bioreactor 4. The magnetic particles are provided in a fluid suspension, for example, in water or other medium.

In other examples, the fluid delivered to the bioreactor 4 by the delivery consumable 5b comprises a virus suspension. Viruses, in suspension, may be provided to the bioreactor 4 to reprogram cells within the bioreactor 4. The viruses are provided in a fluid suspension, for example, in water or other medium.

In examples, the vial 22 is sized to hold up to about 20 ml of fluid, for example, up to about 15 ml of fluid, for example, up to about 13 ml of fluid. In one example, the vial 22 is sized to hold up to about 10 ml of fluid and some air, for example, 3 ml of air. The vial 22 may include markings, for example, gradations, indicating the volume.

In examples, the vial 22 is made from glass. Glass may be beneficial to prevent magnetic particles or viruses from sticking to the vial 22.

In examples, the fluid delivery consumable 5b is storable at temperatures as low as −800 C.

Throughout the description and claims of this specification, the words "comprise" and "contain" and variations of them mean "including but not limited to," and they are not intended to (and do not) exclude other components, integers or steps. Throughout the description and claims of this specification, the singular encompasses the plural unless the context otherwise requires. In particular, where the indefinite article is used, the specification is to be understood as contemplating plurality as well as singularity, unless the context requires otherwise.

Features, integers, characteristics or groups described in conjunction with a particular aspect, embodiment or example of the disclosure are to be understood to be applicable to any other aspect, embodiment or example described herein unless incompatible therewith. All of the features disclosed in this specification (including any accompanying claims, abstract and drawings), and/or all of the steps of any method or process so disclosed, may be combined in any combination, except combinations where at least some of such features and/or steps are mutually exclusive. The disclosure is not restricted to the details of any foregoing embodiments. The disclosure extends to any novel one, or any novel combination, of the features disclosed in this specification (including any accompanying claims, abstract and drawings), or to any novel one, or any novel combination, of the steps of any method or process so disclosed.

The invention claimed is:

1. A fluid delivery consumable for delivering a fluid dose to a bioreactor, the fluid delivery consumable comprising:
   a vial for holding the fluid dose, the vial comprising a first end and a second end opposite of the first end, and the vial defining an outlet in the first end and an opening in the second end;

a plunger engaged with the opening at the second end and operable to urge the fluid dose toward the outlet;

a gaiter sealingly attached to the vial and the plunger to provide a sealed cover for the plunger, wherein the gaiter surrounds the plunger between the second end of the vial and a top end of the plunger; and a connector comprising an end connected to and extending from the first end of the vial, the connector being attachable to the bioreactor and adapted to transfer the fluid dose from the vial to the bioreactor when the plunger is operated to urge the fluid dose out of the outlet of the vial.

2. The fluid delivery consumable of claim 1, further comprising a seal arranged within the outlet of the vial, wherein the seal seals the outlet.

3. The fluid delivery consumable of claim 2, wherein the connector comprises a hollow needle and an actuator, and wherein the actuator is operably connected to the hollow needle to move the hollow needle to pierce the seal to permit fluid flow from the vial through the hollow needle.

4. The fluid delivery consumable of claim 3, wherein the connector comprises a housing, the hollow needle mounted in the housing, wherein the housing comprises a first housing portion and a second housing portion, and wherein the actuator is operably connected to the housing to collapse the first housing portion relative to the second housing portion, wherein the first housing portion is adapted to collapse relative to the second housing portion to move the hollow needle to pierce the seal.

5. The fluid delivery consumable of claim 4, wherein the hollow needle is adapted to engage the bioreactor when the first housing portion collapses relative to the second housing portion while the connector is attached to the bioreactor.

6. The fluid delivery consumable of claim 5, wherein the connector further comprises an end seal disposed at an end of the housing opposite the end of the connector connected to the vial, and wherein the hollow needle is arranged to pierce the end seal when the first housing portion is collapsed relative to the second housing portion.

7. The fluid delivery consumable of claim 1, further comprising a collar attached to the first end of the vial, wherein the collar surrounds the outlet of the vial, and wherein the connector is attached to the collar.

8. The fluid delivery consumable of claim 7, further comprising a lock ring comprising a ring portion and a plurality of tangs extending from the ring portion, wherein the plurality of tangs are arranged to wedge between the vial and the collar so as to secure the collar to the vial.

9. The fluid delivery consumable of claim 7, wherein each of the collar and the connector comprise a threaded portion, and wherein the connector is threadingly attached to the collar by the respective threaded portion.

10. The fluid delivery consumable of claim 9, wherein one of the collar or the connector comprises a clip member arranged to engage the other of the collar or the connector to prevent detachment of the connector from the collar.

11. The fluid delivery consumable of claim 1, wherein the gaiter comprises a collapsible wall.

12. The fluid delivery consumable of claim 11, further comprising a cap attached to the top end of the plunger, the gaiter being attached to the cap, and wherein a first end of the collapsible wall that attaches to the cap is larger than a second end of the collapsible wall that attaches to the vial such that the gaiter comprises a frustrum-shaped collapsible wall.

13. The fluid delivery consumable of claim 12, wherein the frustrum-shaped collapsible wall comprises at least one inward fold towards the plunger and at least one outward fold away from the plunger.

14. The fluid delivery consumable of claim 1, wherein the plunger comprises a piston adapted to seal against an internal surface of the vial.

15. The fluid delivery consumable of claim 1, wherein the connector is integrally formed with the vial.

* * * * *